United States Patent [19]

Harmenberg et al.

[11] Patent Number: 5,571,798
[45] Date of Patent: Nov. 5, 1996

[54] SYNERGISTIC ANTIVIRAL NUCLEOSIDE COMBINATIONS

[76] Inventors: Johan Harmenberg, Karlavagen 94, S-115 22 Stockholm; Britta Wahren, Fritiofsvagen 10, S-182 64 Djursholm; Bo Oberg, Askvagen 27, S-752 52 Uppsala, all of Sweden

[21] Appl. No.: 354,891

[22] Filed: Dec. 9, 1994

Related U.S. Application Data

[63] Continuation of Ser. No. 793,383, filed as PCT/SE90/00487, Jul. 10, 1990 published as WO91/01137, Feb. 7, 1991, abandoned.

[30] Foreign Application Priority Data

Jul. 19, 1989 [SE] Sweden .................................. 8902568

[51] Int. Cl.$^6$ ..................................................... A61K 31/70
[52] U.S. Cl. .................... 514/45; 514/46; 514/49; 514/50; 514/885; 514/922; 536/27.14; 536/28.2
[58] Field of Search ............................... 514/45, 46, 219, 514/50, 885, 922, 49; 536/27.14, 28.2

[56] References Cited

U.S. PATENT DOCUMENTS

| | | | |
|---|---|---|---|
| 4,681,933 | 7/1987 | Chu et al. | 514/49 |
| 4,724,232 | 2/1988 | Rideout et al. | 514/50 |
| 4,861,759 | 8/1989 | Mitsuya et al. | 514/46 |
| 4,879,277 | 11/1989 | Mitsuya et al. | 514/49 |
| 4,880,782 | 11/1989 | Eckstein et al. | 514/45 |
| 4,904,770 | 2/1990 | Starrett, Jr. et al. | 536/28.2 |
| 4,908,440 | 3/1990 | Sterzycki et al. | 536/27.14 |
| 5,026,687 | 6/1991 | Yarchoan et al. | 514/45 |
| 5,059,418 | 10/1991 | Soike | 514/49 |
| 5,122,517 | 6/1992 | Vince et al. | 514/50 |
| 5,234,913 | 8/1993 | Furman, Jr. et al. | 514/49 |

FOREIGN PATENT DOCUMENTS

| | | | |
|---|---|---|---|
| 8800050 | 1/1988 | WIPO | 514/45 |

OTHER PUBLICATIONS

Science, vol. 260, "AIDS, The Unanswred Questions", features editor John Benditt, pp. 1253–1293, 28 May, 1993.
Current Topics in AIDS, vol. 2, "Chapter 112–Strategies for the Treatment of HIV Infection," pp. 235–262, (1989) Mildvan.
Antiviral Chemistry & Chemotherapy (1990) 1(5), 299–306: B. Lundgren et al. Acute Infection of cynomolgus monkeys with Simian immunodeficiency.
Journal of Acquired Immune Deficiency Syndromes 1:257–266, 1988: Bo Oberg "Antiviral Therapy".

Primary Examiner—James O. Wilson
Attorney, Agent, or Firm—Birch, Stewart, Kolasch and Birch, LLP

[57] ABSTRACT

An antiviral composition comprising in combination an effective antiviral amount of 3'-fluoro-2',3'-dideoxy nucleoside compound I of the formula

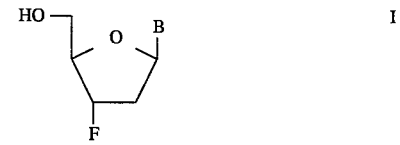

wherein B is adenine, thymine, guanine, cytosine, inosine, uracil, 5-ethyluracil, 2,6-diaminopurine; and an effective antiviral amount of 2',3'-dideoxy nucleoside compound II of the formula

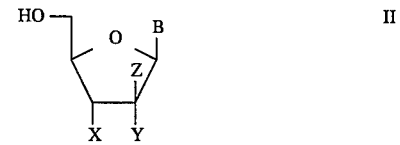

wherein X is N$_3$ or H or together with Y forms an additional carbon-carbon bond, Y and Z are independently H, OH or F, and B is adenine, thymine, guanine, cytosine, inosine, uracil, 5-ethyluracil, 2,6-diaminopurine, and a physiologically acceptable carrier.

3 Claims, 3 Drawing Sheets

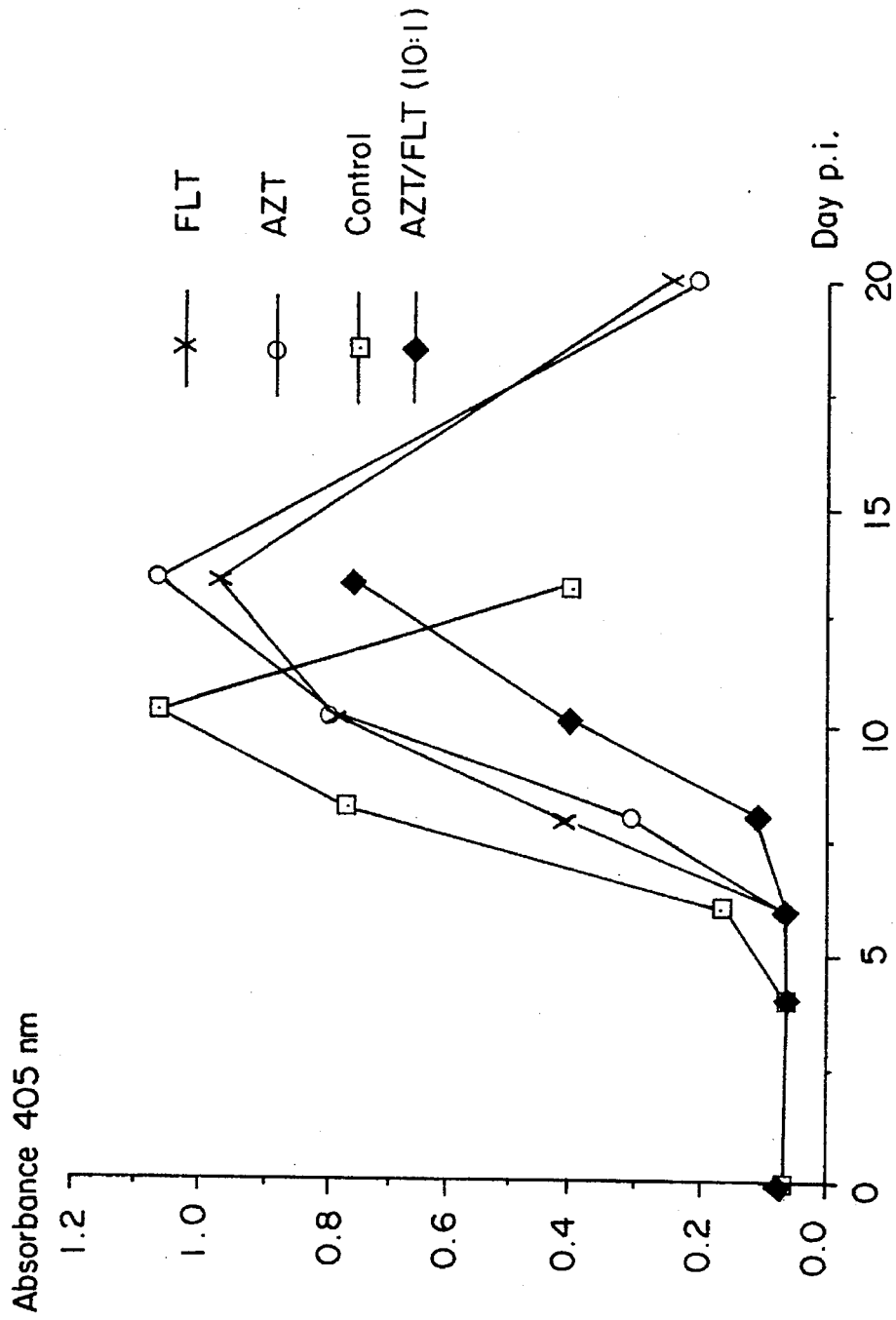

SYNERGISTIC ANTIVIRAL NUCLEOSIDE COMBINATIONS

This application is a continuation of application Ser. No. 07/793,383 filed as PCT/SE90/00487, Jul. 10, 1990 published as WO91/01137, Feb. 7, 1991, now abandoned.

FIELD OF THE INVENTION

The present invention is related to a therapeutic composition comprising a synergistic antiviral combination of a 3'-fluoro-2',3'-dideoxynucleoside and another antiviral 2',3'-dideoxynucteoside for the treatment of infections caused by viruses using reverse transcriptase for replication. In particular it relates to a composition comprising a combination of 3'-fluoro-3'-deoxythymidine (FLT) and 3'-azido-3'-deoxythymidine (AZT) for the treatment of AIDS and HIV infections.

BACKGROUND OF THE INVENTION

Viruses using the enzyme reverse transcriptase for replication are retroviruses and also hepatitis B virus (HBV), which latter contains a specific DNA polymerase required for vital replication. This DNA polymerase also acts as a reverse transcriptase during the replication of HBV DNA via an RNA intermediate.

Infections by a retrovirus referred to as HIV [(Human Immuno Deficiency Virus, formerly known as Human T-cell lymphotropic Virus (HTLV-III) or Lymphadenopathy Associated Virus (LAV)] finally result in AIDS, the Acquired Immuno Deficiency Syndrome, which is characterized by a profound immunodeficiency due to low numbers of lymphocyte-T-helper cells, which are the targets for HIV (also called HTLV-III/LAV) infection. Other retroviruses affecting humans are HTLV-I and II and examples of retroviruses affecting animals are feline leukemia virus (FLV) and equine infectious anaemia virus (EIAV) and simian immunodeficiency virus (SIV).

Hepatitis B virus infections cause severe disease such as acute hepatitis, fulminant hepatitis and chronic hepatitis in a considerable number of persons. It is estimated that there are 200 million patients with chronic hepatitis B in the world. A considerable number of the chronic cases progress to liver cirrhosis and liver tumours. In some cases the hepatitis infections also take a rapid and severe course as in fulminant hepatitis with about 90% mortality. At present there is no known effective treatment against hepatitis B infections.

It is also believed that multiple sclerosis, psoriasis and tropical spastic paraparesis are due to an infection with retroviruses, however, not yet identified.

PRIOR ART

Today only one drug, 3'-azido-3'-deoxythymidine, that is AZT (U.S. Pat. No. 4,724,232), has been licensed for use against AIDS. AZT slows down the progress of the disease and causes an increased survival in patients with AIDS and AIDS-related complex. However, side effects are severe and often require cessation of treatment. The use of AZT in asymptomatic patients is being studied with the hope to decrease the rate of progression of the HIV infection to AIDS.

Another compound showing activity in cell culture against HIV is 3'-fluoro-3'-deoxythymidine, that is FLT (WO 88/00050), a close structural analogue to AZT.

The mechanism of action of AZT and FLT seems to be a phosphorylation by cellular enzymes to 5'-triphosphates which act as inhibitors of HIV reverse transcriptase.

There is a clear need for new anti-HIV drugs with less toxicity than AZT and several new compounds are being evaluated. It has also been shown that combinations of compounds with different modes of action in cell culture can cause synergistic effects against HIV (Öberg, B., Journal of Acquired Immune Deficiency Syndromes 1:257–266, 1988). Compounds showing synergy against HIV in cell culture have been those acting in different ways such as AZT plus foscarnet and AZT plus interferon. Combinations of compounds with structural and presumably mechanistic similarity to AZT such as ddT, d4T and ddC have shown additive effects with AZT against HIV in cell cultures.

DISCLOSURE OF THE INVENTION

It has suprisingly been found that a combination of FLT and another inhibitor of reverse transcriptase shows a synergistic effect against HIV in cell culture and also surprisingly that the compounds, FLT and AZT, show antagonistic effects with respect to cellular toxicity.

A synergistic antiviral effect of FLT and AZT was also found against simian immunodeficiency virus in monkeys and this is the first in vivo synergistic effect against an immuno deficiency virus. This model is closely similar to HIV infection in humans (Lundgren et al., submitted for publication to Antimicrobial Agents and Chemotherapy, 1989) and has a high probability of predicting clinical efficacy.

The high degree of similarity between the reverse transcriptase of HIV and other human and animal retroviruses as well as hepatitis B virus makes it probable that combinations of FLT and other similar inhibitors of reverse transcriptase have synergistic effects also against infections by these viruses.

The present invention is directed to a therapeutic composition comprising a combination of a 3'-fluoro-2'-3'-dideoxynucleoside compound I of the formula

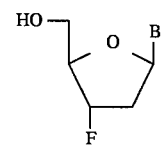

wherein B is adenine, thymine, guanine, cytosine, inosine, uracil, 5-ethyluracil, 2,6-diaminopurine; and a 2',3'-dideoxynucleoside compound II of the formula

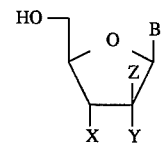

wherein X is $N_3$ or H or together with Y an additional carbon-carbon bond, Y and Z are independently H, OH or F, and B is adenine, thymine, guanine, cytosine, inosine, uracil, 5-ethyluracil, 2,6-diaminopurine, in a ratio giving a synergistic antiviral effect.

The compound I can be selected from the following compounds

3'-fluoro-2',3'-dideoxy adenosine
3'-fluoro-3'-deoxythymidine (FLT)

3'-fluoro-2',3'-dideoxyguanosine
3'-fluoro-2',3'-dideoxycytidine
3'-fluoro-2',3'-dideoxyinosine
3'-fluoro-2',3'-dideoxyuracil
3'-fluoro-2',3'-dideoxy-5-ethyluracil
3'-fluoro-2',3'-dideoxy-2,6-diaminopurine Said compounds all show antiviral effect to some extent.

A preferred compound II showing antiviral effect is a compound of the formula IIa

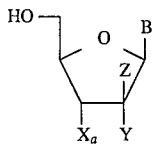

wherein $X_a$ is H or together with Y an additional carbon-carbon bond and B, Y and Z are as defined above.

As examples can be mentioned

2',3'-dideoxyadenosine (ddA)
2',3'-dideoxythymidine (ddT)
2',3'-dideoxyguanosine (ddG)
2',3'-dideoxycytidine (ddC)
2',3'-dideoxyinosine (ddI)
2',3'-dideoxythymidiene (d4T)

Another preferred compound II is a compound of the formula IIb

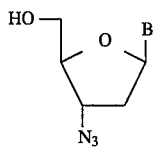

wherein $B_b$ is thymine, uracil or 5-ethyluracil, that is

3'-azido-3'-deoxythymidine (AZT)
3'-azido-2',3'-dideoxyuridine (AZU)
3'-azido-2',3'-dideoxy-5-ethyluridine (CS85)

A preferred composition according to the invention comprises a combination of 3'-fluoro-3'-deoxythymidine and 3'-azido-3'-deoxythymidine.

In order to obtain a synergistic effect the molar ratio of the compound I to compound II should generally be chosen in the range of 50:1 to 1:50.

In the preferred composition comprising a combination of FLT and AZT the range of FLT:AZT giving a synergistic effect is 10:1 to 1:20, with an optimal molar ratio of about 1:1. to 1:10.

In clinical practice the composition of the invention will normally be administered orally, by injection or by infusion in the form of a pharmaceutical preparation comprising the active ingredients in the form of the original compound or optionally in the form of a pharmaceutically acceptable salt thereof, in association with a pharmaceutically acceptable carrier which may be a solid, semi-solid or liquid diluent or an ingestible capsule. The two compounds may also be used without carrier material. As examples of pharmaceutical preparations may be mentioned tablets, dragées, capsules, granulates, suspensions, elixirs, syrups, solutions, etc. Usually the active substances will comprise between 0.05 and 20% for preparations intended for injection and between 10 and 90% for preparations intended for oral administration.

In the treatment of patients suffering from retrovirus infections especially HIV or hepatitis B virus infections, it will be preferred to administer the composition by any suitable rout including the oral, parenteral and rectal route. The parenteral route includes subcutaneous, intramuscular, intravenous and sublingual administration. The topical route includes buccal and sublingual administration. The dosage at which the active ingredients are administered may vary within a wide range and will depend on various factors such as the severity of the infection, the age of patient, etc., and may have to be individually adjusted. As a possible range for the amount of the compounds of the composition of the invention or a physiologically acceptable salt thereof to be administered per day may be mentioned from about 0.1 to about 100 mg/kg body weight of each compound. A preferred composition for example comprises 0.1–1 mg FLT/kg·d in combination with 1–10 mg AZT/kg·d.

BRIEF DESCRIPTION OF THE DRAWINGS

FIG. 3 shows the synergistic effect of FLT and AZT on SIV infection in cynomolgus monkeys.

EXPERIMENTAL TESTS

Figure 1:
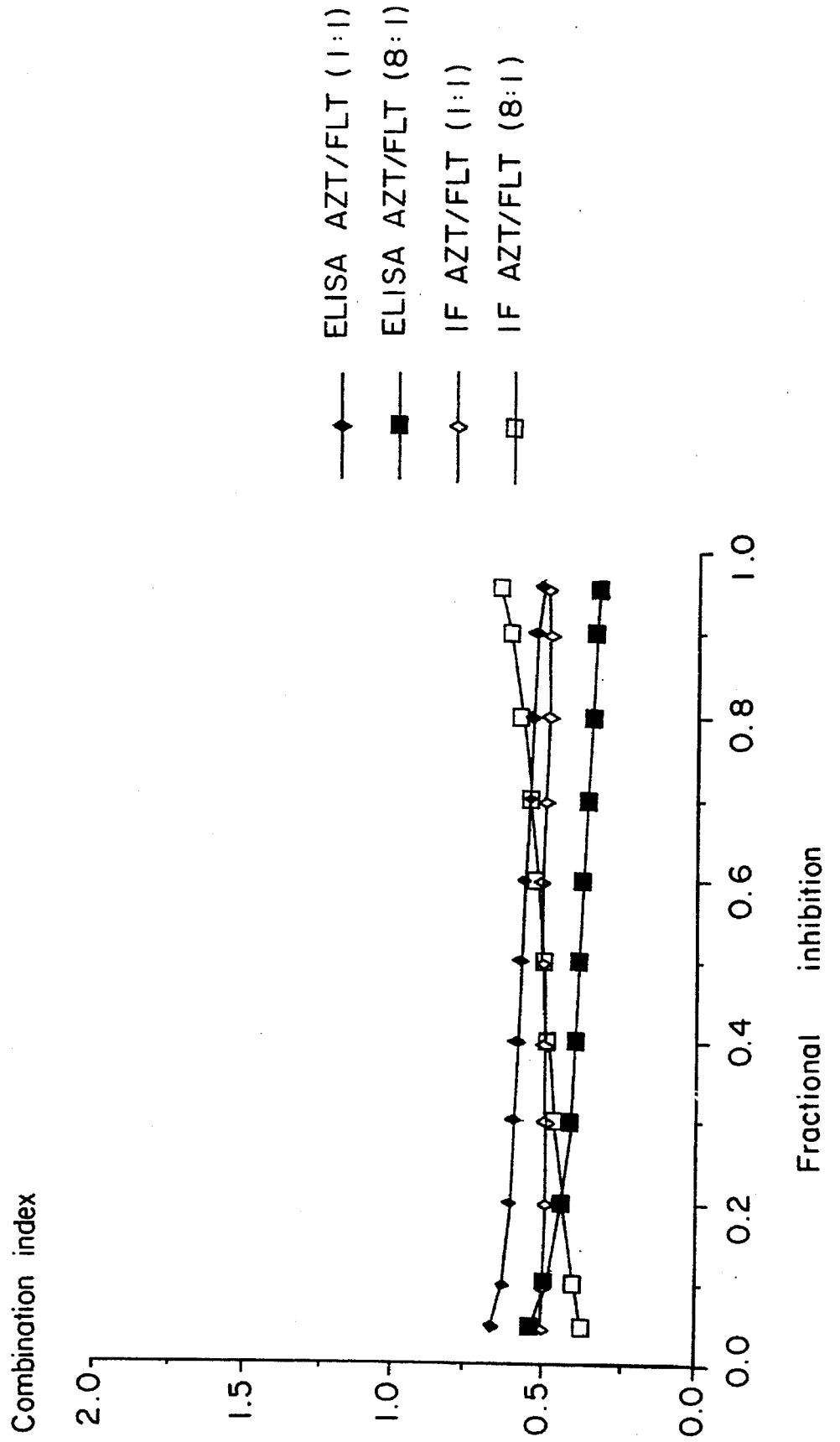
FIG. 1 shows the combination index of anti-HIV effects in cell cultures of fixed mixtures of AZT and FLT at different fractional inhibitions.

The synergistic antiviral effect as well as the cytotoxicity of the combination of the invention is demonstrated in the following tests.

Effect of AZT, FLT and a combination of AZT and FLT in cell culture

Materials and methods

Determination of HIV inhibition. H9 cells (a human CD4+ lymphoid cell line) were grown in suspension in RPMI-1640 medium supplemented with 10% heat-inactivated fetal calf serum and antibiotics. HIV-1 was obtained from the culture supernatant fluid of persistently HIV-infected H9 cells (H9HTLV-IIIB) and stored in 20% fetal calf serum in medium at −70° C. until used. The inhibitory effects of compounds on HIV-replication was determined as follows. Uninfected H9 cells in 0.5 ml ($2\times10^5$ cells/ml) were seeded in 24-well microplates (Costar, Cambridge, Mass.) together with 0.5 ml of medium containing various concentrations of AZT and/or FLT. Infected cells without antiviral compounds were cultivated as a control. Immediately after mixing cells and drugs, 1 ml of HIV of two different concentrations (giving 50–60% and 30–40% infected cells, respectively, after 6 days in culture) was added to each well, giving a total volume of 2 ml. The cultures were incubated at 37° C. in 5% $CO_2$ in air for 6 days without medium change. After incubation, HIV antigen content was measured in the cells by immunofluorescence assay (IFA) and in supernatants by enzyme-linked immunosorbent assay (ELISA).

Immunofluorescence (IF). For IF, cells from each well were washed, spotted onto 8-well slides and allowed to air dry, then fixed in cold (−20° C.) methanol. Human anti-HIV antiserum (containing IgG to all major HIV components) was added and incubated for 30 min in a humid chamber at 37° C. The slides were washed in phosphate buffered saline (PBS; with $Ca^{2+}$ and $Mg^{2+}$) and a fluorescein-isothiocyanate (FITC)-labelled sheep anti-human IgG (all reagents from National Bacteriological Laboratory, Stockholm) was added and incubated for 30 min at 37° C. After washing and counterstaining with Evan's blue, the slides were examined using a fluorescence microscope and the percentage of immunofluorescence positive cells was quantified. The concentration which inhibited vital antigen production by 50% ($IC_{50}$) was calculated.

ELISA. To measure the mounts of HIV antigen in culture supernatants, a sensitive sandwich ELISA (able to detect 20 pg of p24/ml) was used. 100 μl of the serially diluted supernatants from each well were incubated overnight at room temperature in 96-well microplates (Nunc, Aarhus, Denmark) coated with human anti-HIV IgG. After washing, 100 μl of two horse radish-peroxidase (HRPO)-conjugated mouse monoclonal antibodies (Mab) against HIV p24 antigen was added and incubated for 2 h at 37° C. The plates were washed and 100 μl of the substrate ortho-phenylenediamine dihydrochloride (ODP; Dakopatts, Glostrup, Denmark) was added. After 30 min incubation at room temperature the reaction was terminated with 100 μl of 2.5M $H_2SO_4$. The absorbance at 490 nm was measured in a Dynatech MR 600 (Arlington, Va.). All tests were performed in duplicate. A HIV antigen standard was included on each plate every time. The concentration which inhibited vital antigen production by 50% ($IC_{50}$) was calculated.

Cytotoxicity measurement. Uninfected CEM cells (a CD4+ human T cell line) were incubated in the presence of different concentrations of AZT or FLT or combinations of AZT/FLT. After three days of incubation, viable cells were counted in a volume distribution analyzer (VDA 140, Analys-instrument AB, Stockholm, Sweden). The results were compared to control cells incubated without antiviral drug. The concentration required to inhibit cell proliferation by 50% ($CIC_{50}$) was calculated using computer program.

Data calculations. All results from cell cultures were analyzed using a computer program (developed by Dr. Johan Harmenberg) for Apple, MacIntosh. The program follows the median effect principle as published by Chou and Talalay, Adv. Enz. Reg. 22:27–55, 1984. The program yields 50% inhibition concentrations, $IC_{50}$, $CIC_{50}$, and combination index (C.I.). C.I. of 1 indicates that two drugs exhibit additive activities. C.I.<1 indicates synergy and C.I.>1 indicates antagonism. The fraction affected (Fa) is defined as the fraction of infected cells (0–1) inhibited by the drug. An Fa=1 means 100% inhibition and Fa=0 means 0% inhibition. In the median effect principle a fixed ratio between the concentrations of the two drugs is used. The antiviral or cytotoxic activity of different concentrations at the same fixed ratio was then analyzed using the computer program (Harmenberg J., Åkesson-Johansson A., Vrang L. and Cox S., Inhibition of human immunodeficiency virus in vitro by combinations of 3'-azido- 3'-deoxythymidine and 3'-fluoro-3'-deoxythymidine, Department of Virology, National Bacteriological Laboratory, S-105 21 Stockholm, Sweden).

Effect of AZT, FLT and combinations of AZT and FLT against HIV in H9 cell culture Antiviral drug effects have been studied using anti-p24 ELISA of cellular supernatants or whole cell immunofluorescence (IF) using human anti-HIV antiserum. FLT and AZT were tested on cell cultures at concentrations starting at 0.000065 μM and increased in twofold steps up to 0.256 μM. The molar ratios of FLT and AZT were selected from $IC_{50}$ in cell culture experiments. The ratios 1:8 and 1:1 were used in the combination experiments. The methods have been described by Koshida et al., Antimicrob. Agents and Chemother. 33:778–780, 1989.

Even though the two methods measure different aspects of the HIV infection, the results were similar. FLT alone, in all experiments showed at least ten-fold higher antiviral activity than AZT alone. The results are given in Table 1.

The combination experiments all showed antiviral synergy as is also indicated by the C.I. in FIG. 1. The C.I.'s for the two combinations with IF or ELISA techniques ranged from 0.34 to 0.67. The two methods (ELISA and IF) to study antiviral effects did not differ substantially in this respect. A C.I. of less than 1 indicates a synergistic effect.

Cellular growth inhibition by FLT and AZT

Cellular growth was studied using volume distribution analyzer for cell counting. FLT showed more than ten-fold lower $CIC_{50}$ value compared to AZT. See Table 1.

Figure 2:
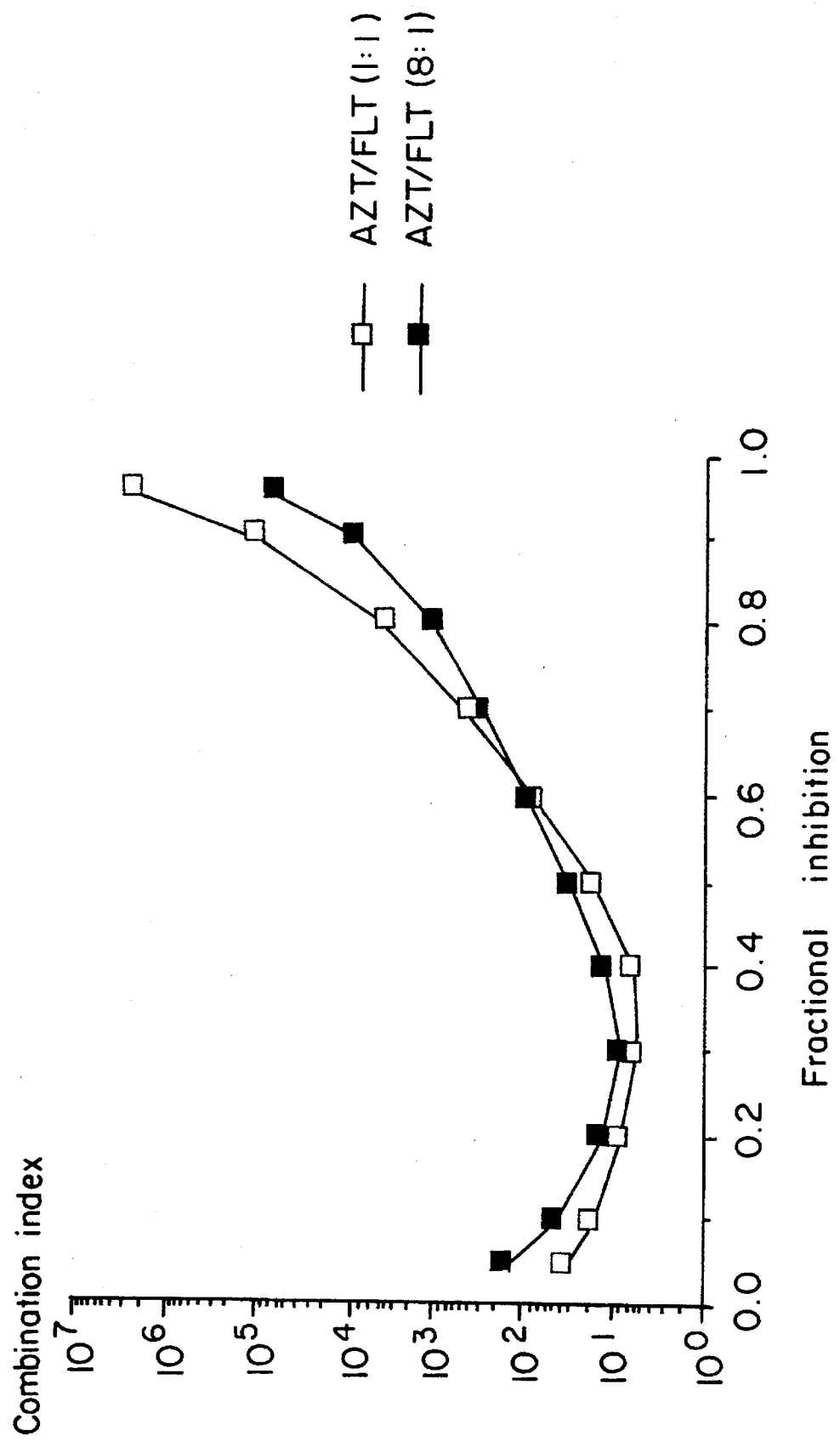
FIG. 2 shows the combination index of cellular growth inhibitions of fixed mixtures of AZT and FLT at different fractional inhibitions.

The combination index of cellular growth inhibition of the two mixtures of AZT and FLT, that is 1:1 and 8:1, showed an antagonistic relationship, as shown in FIG. 2.

TABLE 1

Anti-HIV and cytotoxic effect of AZT, FLT and combinations of AZT and FLT in cell culture.

| Substance | HIV-Inhibition $IC_{50}$, μM | | Cytotoxicity C $IC_{50}$, μM | Therapeutic Index $CIC_{50}/IC_{50}$ | |
|---|---|---|---|---|---|
| | ELISA | IF | | ELISA | IF |
| AZT | 0.038 | 0.057 | 88.5 | 2323 | 1549 |
| FLT | 0.003 | 0.002 | 5.70 | 1816 | 2863 |
| AZT:FLT (1:) | 0.003 | 0.002 | 27.7 | 8666 | 14742 |
| AZT:FLT (8:1) | 0.007 | 0.007 | 63.5 | 9625 | 9169 |

The results show a synergistic effect of FLT and AZT against HIV replication in cell cultures and also that the combination has an antagonistic effect against cell growth. This means that the therapeutic index, that is the ratio of cellular toxicity to antiviral effect, $CIC_{50}:IC_{50}$, of the combination is higher than for each component.

Effect of AZT, FLT and a combination of AZT and FLT against SIV in macaques

The general design of the evaluation of combinations of FLT and AZT in monkeys infected with simian immunodeficiency virus ($SIV_{SMM}$) followed the method of Lundgren et al., loc. cit. 1989. 4 monkeys were used in each treatment group and 4 monkeys in the control group. Treatment started 8 hours prior to virus inoculation and was given 3 times a day as subcutaneous injections at the dose levels of 3×0.250 mg/kg/day of FLT, 3×2.50 mg/kg/day of AZT and 3×(0.125 mg/kg/day of FLT+1.25 mg/kg/day of AZT). The compounds were given for 10 days and the appearance of SIV p24 antigen in monkey serum was followed for 40 days by a modified Abbott HIV p24 test.

FIG. 3 shows the effects of FLT, AZT and a combination of FLT and AZT against $SIV_{SMM}$ infection in *Macaca fasicularisis*. At a dose level of 3×0.25 mg/kg of FLT and 3×2.5 mg/kg AZT the same antiviral effect was obtained as observed in a delay in p24 antigen appearance. When half the of respective concentrations of FLT (3×0.125 mg/kg) and AZT (3×1.25 mg/kg) were used as a combined treatment, a synergistic effect on SIV replication was seen in the delay in p24 antigen appearance instead of the added effect expected.

We claim:

1. An antiviral composition which consists essentially of an effective anti-retroviral synergistic amount of 3'-fluoro-3'-deoxythymidine and an effective anti-retroviral synergistic amount of 3'-azido-3'-deoxythymidine, and a pharmaceutically acceptable carrier.

2. A synergistic antiviral composition which consists essentially of an effective anti-retroviral synergistic amount of 3'-fluoro-3'-deoxythymidine and an effective anti-retroviral synergistic amount of 2',3'-dideoxyinosine; and a pharmaceutically acceptable carrier.

3. A synergistic antiviral composition comprising in combination an effective antiviral synergistic amount of 3'-fluoro-2',3'-dideoxy nucleoside compound I of the formula:

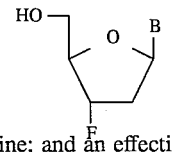

wherein B is guanine; and an effective antiviral synergistic amount of a 2',3'-dideoxy nucleoside selected form the group consisting of 2',3'-dideoxycytidine (ddC), 2',3'-dideoxyinosine (ddI) and 3-azido-3'-deoxythymidine (AZT); and a pharmaceutically acceptable carrier.

* * * * *